United States Patent [19]

Monaghan et al.

[11] Patent Number: 4,695,544
[45] Date of Patent: Sep. 22, 1987

[54] PROCESS FOR THE PREPARATION OF CHOLECYSTOKININ ANTAGONISTS

[75] Inventors: Richard L. Monaghan, Somerset; Michael A. Goetz, Fanwood; Raymond S. Chang, Edison, all of N.J.

[73] Assignee: Merck & Co., Inc., Rahway, N.J.

[21] Appl. No.: 712,046

[22] Filed: Mar. 15, 1985

Related U.S. Application Data

[63] Continuation of Ser. No. 509,883, Jul. 1, 1983, Pat. No. 4,530,790, which is a continuation-in-part of Ser. No. 453,383, Dec. 27, 1982, abandoned.

[51] Int. Cl.$^4$ .......................... C12N 1/14; C12P 17/18; C12R 1/66
[52] U.S. Cl. .................................. 435/119; 435/254; 435/913
[58] Field of Search ................ 435/118, 119, 254, 913

[56] References Cited

U.S. PATENT DOCUMENTS 3,944,470  3/1976  Diehl et al. .......................... 435/188

FOREIGN PATENT DOCUMENTS 0722946  3/1980  U.S.S.R. .............................. 435/913

OTHER PUBLICATIONS

Chien et al.; "Microbial Transformations of Natural Antitumor Agents: Use of Solubilizing Agents to Improve Yields of Hydroxylated Ellipticines"; *Applied and Environmental Microbiology*, vol. 40, No. 4, Oct. 1980, pp. 741–745.

*Primary Examiner*—Thomas G. Wiseman
*Assistant Examiner*—Elizabeth C. Weimar
*Attorney, Agent, or Firm*—Samuel B. Abrams; Hesna J. Pfeiffer

[57] ABSTRACT

A process for preparing the compound having Formula I and several minor related compounds.

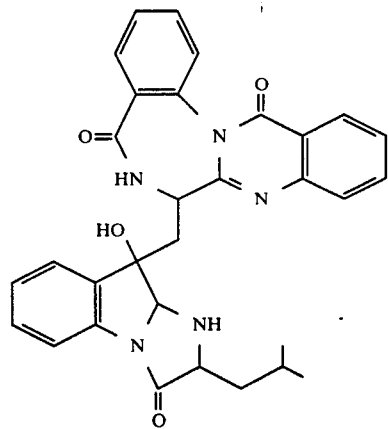

The compound of Formula I and the several minor related compounds are antagonists of cholecystokinin (CCK). CCK antagonists are useful in the treatment and prevention of disorders of the gastrointestinal, central nervous and appetite regulatory systems of animals, especially humans.

6 Claims, 7 Drawing Figures

PROCESS FOR THE PREPARATION OF CHOLECYSTOKININ ANTAGONISTS

This is a continuation of application Ser. No. 509,883, filed July 1, 1983, now U.S. Pat. No. 4,530,790, now U.S. Pat. No. 4,530,790, which in turn is a continuation-in-part of application Ser. No. 453,383, filed Dec. 27, 1982, now abandoned.

BACKGROUND OF THE INVENTION

Cholecystokinin (CCK) is a neuropeptide composed of thirty three aminoacids. See: Mutt and Jorpes, *Biochem. J.* 125 678 (1971). CCK exists in both gastrointestinal tissue and the central nervous system. CCK is believed to play an important role in appetite regulation and CCK may be a physiological satiety hormone. CCK reportedly co-exists with dopamine in certain mid-brain neurons and thus may additionally play a role in the functioning of dopaminergic systems in the brain, as well as, serving as a neurotransmitter in its own right. See: A. J. Prange et al., "Peptides in the Central Nervous System", *Ann. Repts. Med Chem.* 17 31, 33 (1982) and references cited therein, J. A. Williams, *Biomed. Res.* 3 107 (1982) and J. E. Morley, *Life Sci.* 30 479 (1982). CCK antagonists are useful in the treatment and prevention of disorders of the gastrointestinal, central nervous and appetite regulatory systems of animals, especially humans.

SUMMARY OF THE INVENTION

The compound having Formula I and several minor related compounds are produced by the controlled aerobic fermentation of *Aspergillus alliaceus* Thom and Church ATCC No. 20655 or ATCC No. 20656.

The compound of Formula I and the minor related compounds are antagonists of cholecystokinin (CCK). CCK antagonists are useful in the treatment and prevention of disorders of the gastrointestinal, central nervous and appetite regulatory systems of animals, especially humans.

The preparation and isolation of the compound of Formula I is described. Also described is the in vitro activity of the compound of Formula I as an antagonist of CCK.

DETAILED DESCRIPTION

The compound of Formula I and several minor related compounds are produced by the controlled aerobic fermentation of a strain of *Aspergillus alliaceus* Thom and Church, preferably, ATCC No. 20655 or ATCC No. 20656.

The microorganism ATCC No. 20655 was isolated from soil and a sample of this living organism has been deposited without restriction in, and made a part of, the American Type Culture Collection, Rockville, Maryland, from which it is available under Accession Number ATCC No. 20655. The microorganism ATCC No. 20656 is a naturally occurring subisolate of ATCC No. 20655. It should be understood that the availability of these cultures do not constitute the granting of a license to practice the invention claimed herein.

An examination of the cultural and morphological characteristics of *Aspergillus alliaceus* Thom and Church, ATCC No. 20655 was made according to Kenneth B. Raper and Dorothy S. Fennel's "The Genus Aspergillus", R. E. Krieger Publishing Co., Huntington, N.Y. (1977).

The cultural characteristics of *Aspergillus alliaceus* Thom and Church, ATCC No. 20655 are as follows:

Colonies on Czapek's solution agar 5.5–6.5 cm in diameter in two weeks at 25° C. consist of a white to pale yellowish mycelium bearing relatively few conidial structures and variable numbers of incipient sclerotia, the latter at first white to silver in color but becoming black in age, ranging from globose to vertically elongate and measuring up to 1.0 mm in diameter (occasionally more); conidial heads variable in size, basically globose but with larger structures later forming divergent columns of conidia, mature heads up to 500–700 μl in diameter, yellow-orange to buff in color, borne on conidio phore of variable dimensions up to 2–3 mm in length by 8–15 μm in width with walls smooth and comparatively heavy; vesicles globose, mostly 30–60

μm wide and bearing metulae over the entire surface; metulae commonly 10–15×3–5 μm, each bearing 4–8 phialides 8–12×1.5–2.5 μm; conidia yellowish, oval to subglobose, smooth-walled, mostly 3.0–3.5×2.5–3.0 ascospores.

Colonies on malt agar growirng more rapidly, 6.5–7.0 cm in two weeks, somewhat flocculent, with conidial structures usually somewhat more abundant than on Czapek and sclerotia relatively fewer in number.

Colonies on hay infusion agar comparatively thin, heavily sporing, conidiophores generally short and conidial heads generally small and not splitting except in larger structures near colony margins. Sclerotia not produced.

Further Observations:

(1) The sclerotia in some isolates of *A. alliaceus* have been found to contain cleistothecia with asci and ascospores after aging for several months; sclerotia of other isolates have failed to show the sexual stage at any age. The oldest sclerotia examined for this strain were nine weeks—too early to show this stage if the potentiality exists. See Fennell and Warcup in Mycologia 51: 411 (1959).

(2) Colonies vary substantially on different substrates, and individual colonies differ in pattern and composition (of conidial heads and sclerotia) on the same substrate. Those from the lyophil preparation generally showed fewer sclerotia than those from the agar plates furnished.

(3) Additionally, it has been observed that cultures inoculated with relatively clean sclerotia yielded colonies with many more sclerotia than colonies derived from conidia taken from isolated conidial heads. Regrowth in the former case, probably came from vegetative hyphae that accompanied the sclerotia when removed from the parent plate Subisolate ATCC No. 20656 has essentially the same cultural characteristics as ATCC No. 20655.

It is to be understood that for the fermentation production of the compound of Formula I and its several minor related compounds, the present invention is not limited to the use of *Aspergillus alliaceus* Thom and Church, ATCC No. 20655 or ATCC No. 20656. It is especially desired and intended that there be included within the scope of this invention, the use of other natural or artificial mutants produced or derived from the described cultures, or other variants or species of the genus Asperqillus in so far as they can produce the compound of Formula I or any of its several minor related compounds. The artificial production of mutant species or strains of Aspergillus from ATCC No. 20655 or ATCC No. 20656 may be achieved by conventional physical or chemical mutagens, for example, ultraviolet irradiation of the described cultures, or nitrosoguanidine treatment and the like. Recent recombinant DNA techniques such as protoplast fusion, plasmid incorporation, chromosome fragment incorporation and the like may also prove useful.

In a preferred embodiment of the present invention, the compound of Formula I and its several minor related compounds are produced by the controlled aerobic fermentation of the microorganism *Aspergillus alliaceus* Thom and Church, ATCC No. 20655 or ATCC No. 20656. The fermentation should be conducted at a temperature range of from about 20° to 37° C., preferably at about 28° C. Generally, the composition of the assimilable nutrient medium may be varied over a wide range. The essential nutrient ingredients are a carbon source and a nitrogen source. Other essential nutrients are provided via mineral salts such as the chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like.

Typical sources of carbon include; glucose, oils, organic acids, dextrin, starches, glycerol and the like. Typical nitrogen sources include; amino acids, vegetable meals, and extracts (e.g., malts, soy, cotton seed, figs, tomato, corn, etc.), animal viscera, various hydrolysates (e.g., casein, yeast, etc.) and industrial by-products such as lard water and distillers solubles.

The maximum yield of the compound of Formula I can be achieved within about 24 to 200 hours, usually in about 96–144 hours, of fermentation under optimum conditions. The innoculum for the fermentation may be provided from vegetative growth in a medium which supports rapid growth of the microorganism, or directly from spores.

Following fermentation, the accumulated compound of Formula I may be separated from its several minor related compounds and recovered from the broth by conventional chromatographic means.

The fermentation broth is filtered to separate mycelia from liquid supernatant. These are extracted as follows:

A. The supernatant is shaken with an equal volume of a moderately polar solvent, immiscible in water such as; chloroform, ethyl acetate, methyl ethyl ketone, and the like. The layers are allowed to settle; the organic phase contains all of the compound of Formula I initially located within the supernatant.

B. The mycelia are stirred vigorously (homogenized) with several volumes of acetone, ethyl acetate, methyl ethyl ketone or the like. These solvents will dissolve most of the compound of Formula I located within the mycelia.

The combined mycelial and supernatant organic extracts are then concentrated to a small volume under reduced pressure. The resultant mass is subjected to a series of solvent partioning and washing steps. Solvents of choice include petroleum ether, hexane, ether, methylene chloride, methanol and similar solvents Adsorption and partition chromatographies, gel filtration, reversed-phase liquid chromatography and the like may be used, in conjunction witn eluents of proper polarity and solubilizing characteristics to afford the compound of Formula I as an off-white powder.

The several minor components of the fermentation broth may be recovered by a similar application of a series of chromatographic techniques. Four minor components, herein referred to as A, B, C and D have thus far been isolated from the fermentation broth of *Aspergillus alliaceus* Thom and Church, ATCC No. 20655 and 20656. By weight, these minor components, combined, amount to about five weight percent of the isolated compound of Formula I.

A number of different nutrient media may be employed in the fermentatioin of *Aspergillus alliaceus* Thom and Church, ATCC No. 20655 and ATCC No. 20656. Variation of the medium or the microorganism will vary the yield of the compound of Formula I and/or its rate of production. Variation of the medium or the microorganism may also increase or decrease the type and amount of the several minor related compounds present in the broth. The preferred media compositions are set forth in Table I.

TABLE I

Media Composition

| | |
|---|---|
| Medium A | Corn Steep 5 g, Tomato Paste 40 g, Oat flour 10 g, Dextrose 10 g, Trace Element Mix No. 1 10 ml, CaCl$_2$ 2H$_2$O 10 g, Distilled water 1000 ml, pH 6.8 |
| Trace Element Mix No. 1 | Fe SO$_4$7H$_2$O 1 g, MnSO$_4$ 4H$_2$O 1 g, CuCl$_2$2H$_2$O 25 mg, CaCl$_2$2H$_2$O 100 mg, H$_3$BO$_3$ 56 mg, (NH$_4$)$_6$Mo$_7$O$_{24}$4H$_2$O 19 mg, ZnSO$_4$7H$_2$O 200 mg Distilled, deionized water 1000 ml |
| Medium B | Dextrose 4 g, Malt Extract 10 g, Yeast Extract 4 g, Agar 20 g, Distilled water, 1000 ml, pH 7.0 |
| Medium C | Dextrose 1 g, Dextrin 10 g, Beef extract 3 g, Ardamine pH 5 g, NZAmine E 5 g, MgSO$_4$ 7H$_2$O 0.05 g, KH$_2$PO$_4$ 0.182 g, Na$_2$HPO$_4$ 0.190 g, CaCO$_3$ 0.5 g, Distilled water 1000 ml pH7-7.2 |
| Medium D | Tomato Paste 30 g, Corn Meal 10 g, Ardamine pH 5 g, Distilled water 1000 ml, pH 5.0 |
| Medium E | Dextrose 40 g, NaNO$_3$ 5 g, K$_2$HPO$_4$ 1 g, MgSO$_4$ 7H$_2$O 0.5 g, KCl 0.5 g, FeSO$_4$ 7H$_2$O 10 mg, ZnSO$_4$ 7H$_2$O 10 mg, pH to 7.0 with HCl then CaCO$_3$ 10 g L-tryptophan 4 g, Distilled water 1000 ml |
| Medium F | Corn meal 5 g, Ardamine pH 5 g, lard water 5 g, Pharmamedia 20 g, sodium citrate 2 g, L-phenylalanine 2 g, L-tryptophan 2 g, KH$_2$PO$_4$ 2 g, (NH$_4$)$_2$SO$_4$ 1 g, polyglycol P2000 1 ml, distilled water 1000 ml |
| Medium G | Corn steep 0.5%, tomato paste 4.0%, oat flour 1.0%, glucose 1.0%, CaCl$_2$ 1.0%, trace element mix No. 2 1%, Distilled water 1000 ml |
| Trace Element Mix No. 2 | FeSO$_4$7H$_2$O 10 mg, MnSO$_4$4H$_2$O 10 mg, CuCl$_2$2H$_2$O 0.25 mg, CaCl$_2$ 1.0 mg, H$_3$BO$_3$ 0.56 mg, (NH$_4$)$_6$Mo$_7$O$_{24}$4H$_2$O 0.19 mg, ZnSO$_4$7H$_2$O 2.0 mg Distilled, deionized water, 1000 ml |
| Medium H | Tomato Paste 6.0%<br>Corn Meal 2.0%<br>Ardamine pH 1.0%<br>Polyglycol P2000 0.02%<br>Distilled water 1000 ml<br>pH 5.0 |
| Medium I | Tomato Paste 6.0%<br>Corn Gluten Meal 2.0%<br>Ardamine pH 1.0%<br>Polyglycol P2000 0.02%<br>Distilled water 1000 ml<br>pH 5.0 |

The terms "seed" and "production" media are employed as terms of art. Generally, a seed medium supports rapid growth of the microorganism and an aliquot (seed) of this medium is used to inoculate a production medium for a large scale fermentation.

The following examples describe the fermentation production and isolation of the compound of Formula I and its several minor related compounds. These examples are merely illustrative, they are not intended to limit the scope of this invention.

EXAMPLE 1

Fermentation Production

A lyophylization tube of *Aspergillus alliaceus* Thom and Church, ATCC No. 20655 was added under aseptic conditions to 44 ml of medium A in a 250 ml baffled Erlenmeyer flask. The flask was maintained at 28° on a 220 rpm rotary shaker for from 1-3 days. A portion of the growth from this flask was used to inoculate an 18×175 mm agar slant tube containing about 15 ml of medium B. The agar slant tube was incubated at 28° C. for greater than two weeks at which time it was well sporulated. A spore scraping from this incubated tube was used to inoculate 54 ml of medium C in a 250 ml baffled Erlenmeyer flask. The dispensed spore contents in medium C were then used to inoculate 300 ml of medium D in an unbaffled 2 liter Erlenmeyer flask. This flask was incubated for 7 days at 28° C. on a rotary shaker at 150 rpm, after which time the broth was harvested.

EXAMPLE 2

Fermentation Production

A portion of about one half of the surface growth of an agar slant tube prepared as in Example 1, dispersed in sterile water, was used to inoculate 44 ml of medium A minus the CaCl$_2$ in a 250 ml unbaffled Erlenmeyer flask. Medium E may be substituted for the medium A minus the CaCl$_2$. The flask was incubated at 28° C. for 2 days on a 220 rpm rotary shaker. Approximately one half of the flask contents were stored at 4° C. for 1 day and then incubated without agitation at from 24° to 29° C. (room temperature) for 7 days. An equal volume of medium D was then adoed to the flask. Two ml from this flask was then used to inoculate 44 ml of medium D in an unbaffled 250 ml Erlenmeyer flask. This flask was incubated for 7 days at 28° C. on a 220 rpm rotary shaker and harvested.

Example 2 was repeated concurrently 19 times and the harvested broths were combined for isolation of the compound of Formula I as described in Example 3.

EXAMPLE 3

Isolation of Formula I

The combined fermentation broth from Example 2 (900 ml) was centrifuged to separate the mycelia from the broth liquid. The mycelia were extracted by stirring with two successive 450 ml portions of ethyl acetate. The broth liquid was also extracted twice with 450 ml of ethyl acetate.

Thin layer chromatography (tlc) on silica gel (5% MeOH in CH$_2$CL$_2$) showed one major UV active spot ($R_f$=0.6) for the organic extracts of the mycelia and the broth liquid. Reverse phase tlc using a KC$_{18}$ plate and 75% MeOH showed one major UV active spot ($R_f$=0.70).

The mycelial organic extract was evaporated to dryness and the residue was dissolved in 5 ml of methylene chloride containing a trace of methanol. This solution was fractionated on a 100 cc silica gel column packed in hexane-methylene chloride (1:1 v/v). Elution was carried out as follows:
150 ml hexane-CH$_2$Cl$_2$(1:1)
100 ml CH$_2$Cl$_2$
100 ml CH$_2$Cl$_2$-acetone (9:1)
100 ml CH$_2$Cl$_2$-acetone (4:1)

100 ml CH$_2$Cl$_2$-acetone (1:1)
100 ml acetone
100 ml acetone-MeOH (1:1)

Forty fractions (each 20 ml) were collected. Analysis by tlc (silica gel, 5% MeOH in CH$_2$Cl$_2$) indicated which fractions were to be combined. The combinations afforded nine fractions (1–9).

The organic extract of the supernatant was evaporated to dryness and the residue was dissolved in 10 ml methanol containing a trace (1 ml) of methylene chloride. This solution was chromatographed on a 2m×1 inch Sephadex LH-20 gel filtration column eluted with methanol at 5 ml/min. Fractions were collected every 15 ml. UV and tlc analysis indicated which fractions were to be combined. The combinations afforded thirteen fractions (1–13).

Thin layer chromatographic analysis of the fractions from the silica gel and the LH-20 gel filtration columns confirmed the presence of the major component in fraction number 7 (silica) and fractions 5 and 6 (LH-20).

Fraction number 7 (silica) was evaporated to dryness under reduced pressure. The residue thus obtained was dissolved in 1.5 ml of methanolmethylene chloride (95:5 v/v) and fractionated on a reverse phase high pressure liquid chromatography column (9 mm×50 cm) eluting with a gradient of acetonitrile in water (from 40% CH$_3$CN to 100% CH$_3$CN) Five fractions were collected. Fraction number 3 contained 2.5 mg of the purified compound of Formula I.

Combined fractions 5 and 6 (LH-20) were evaporated to dryness under reduced pressure. The residue was taken up in methanol-methylene chloride (95:5 v/v) and fractionated by HPLC as above to yield 15 mg of the compound of Formula I.

EXAMPLE 4

Fermentation Production

*Aspergillus alliaceus* Thom and Church, ATCC No. 20656 was grown in 40 ml of seed medium G (minus CaCL$_2$) in a 250 ml Erlenmeyer flask for eleven days at 28° C. without agitation, to yield a spore suspension.

Two ml of the spore suspension grown above was used to inoculate three 250 ml baffled Erlenmeyer flasks each containing 50 ml of medium G. Each flask was maintained at 28° C., and 150 rpm for 48 hours.

Fifteen ml of the medium G growth described above was used to inoculate three 2 liter non-baffled Erlenmeyer flasks each containing 500 ml of medium H. Each flask was maintained at 28° C. and 150 rpm for 24 hours.

One liter of the medium H growth described above was used to inoculate a 750 liter stainless steel fermenter containing 500 liters of sterilized medium I. This vessel was maintained at 28° C. with an air flow of 15 cfm and agtation of 130 rpm for 24 hours.

Fifty liters of the large scale seed medium I described above was used to inoculate a 750 liter stainless steel fermenter containing 500 liters of sterilized production medium F. This vessel was maintained at 28° C. with an air flow of 15 cfm and agitation of 160 rpm for 120 hours, after which time the broth was harvested.

EXAMPLE 5

Isolation of Formula I

Fermentation broth was filtered through a filtering aid. The broth liquid obtained was extracted once with an equal volume of ethyl acetate. After allowing the layers to settle, the organic layer was collected.

The mycelia were vigorously stirred with two successive equivalent portions of ethyl acetate. After fltration, the organic mycelia extracts were combined with the organic extract of the broth liquid, and the combined solution was evaporated under reduced pressure to an oil.

The oil was treated with 500 ml of ice-cooled petroleum ether; the precipitate that formed was collected by filtration and washed with a fresh 250 ml of petroleum ether. The remaining solids were then stirred with two successive 500 ml volumes of methanol to dissolve the active component. Some inactive, insoluble material was eliminated at this point by filtration. The alcohol solution, containing all the desired component, was evaporated to dryness under reduced pressure at relatively low temperature. The resultant solid residue was triturated with methylene chloride (three successive 200 ml volumes). More insoluble impurities were removed by filtration. The solution was used directly, without further handling, for chromatography.

Adsorption chromatography was used as a first step. The above solution was charged onto a 1 m×5cm column packed with silica gel previously equilibrated with methylene chloride-methanol (96:4, v/v). Elution was carried out with the same solvent; the active compound eluted in approximately 2.4–3.0 column volumes. The active fractions were combined, taken down to dryness under reduced pressure and the solid residue was dissolved in 40 ml of methanol.

Gel filtration chromatography was carried out on this material on a 2 m×5 cm column of Sephadex LH-20 gel equilibrated with methanol. The compound of Formula I eluted between 1.0 and 1.3 column volumes. The appropriate fractions were combined, concentrated and further purified by reversed-phase high pressure liquid chromatography (RP-18 packing 1"×6' column, eluted with 40% acetonitrile in water). The off-white solid material obtained was chromatographically pure as determined by tnin layer chromatography and high pressure liquid chromatography, and was identical to the compound isolated in Example 3.

EXAMPLE 6

Isolation of Formula I

Fermentation broth (17 liters) was filtered through supercell. The filter cake was extracted twice with successive 3 liter portions of ethyl acetate. After evaporation of the solvent, the residue was taken up in 15 ml of methanol and passed at high speed through a 250 cc bed volume of silica gel packed in methylene chloride-acetone (4:1 v/v). After recovery of the fractions containing the compound of Formula I and evaporation of the solvent, the residue was dissolved in 14 ml of methylene chloride-methanol (1:2 v/v) and fractionated on silica gel (250 cc packed in methylene chloride). Elution was carried out witn 250 ml of methylene chloride, followed by 300 ml of methylene chloride-acetone (9:1 v/v) then 300 ml of methylene chloride-acetone 2:1 v/v.

The fractions containing the compound of Formula I were combined. After evaporation of the solvent, the residue was dissolved in 8 ml of methanol and further purified by gel filtration on Sephadex LH-20 (1 inch×2 m column, eluant:methanol). The compound of Formula I was eluted between 0.90 and 1.02 column volumes). The solvent was again evaporated and the residue was re-dissolved in methanol. Final purification was achieved by reversed-phase HPLC (Whatman ODS-3 Magnum-9 column using actnitrile-water 35:65 v/v as eluant. This sample was identical (tlc, HPLC) to the previously isolated samples. This purified sample was used for the structural characterization studies described herein below.

EXAMPLE 7

Isolation of Minor Components A, B and C

Fermentation broth (250 ml) was extracted with an equivalent volume of ethyl acetate by shaking vigorously for 15 minutes. Tne broth was then filtered and the organic layer was evaporated under reduced pressure to dryness.

The residue was dissolved in 15 ml of methylene chloride containing 2.5 volume percent methanol. The solution was fractionated by silica gel chromatography. The column was packed and equilibrated with methylene chloride-methanol (97.5:2.5 v/v). The column was eluted with 200 ml of this solvent mixture followed by 560 ml of methylene chloride-methanol (95:5 v/v). Fractions were analyzed by thin layer chromatography and high performance liquid chromatography.

Components A, B and C were eluted from the column together between 1.2 and 1.5 column volumes.

The compound of Formula I was eluted from the column between 2.3 and 3.0 column volumes.

The fractions containing components A, B and C were combined and evaporated to dryness under reduced pressure. The residue thus obtained was dissolved in 500 l of methanol and further fractionated by reverse phase high performance liquid chromatography (Whatman ODS-3 Magnum 9 column) eluting with 40% by volume $CH_3CN$ in water at 10.0 ml/min.

Component A was obtained pure between 2.3 and 2.6 column volumes of eluate.

Component B was obtained pure between 4.8 and 5.1 column volumes of eluate.

Component C was obtained pure between 5.8 and 6.3 column volumes of eluate.

EXAMPLE 8

Isolation of Minor Component D

Fermentation brotn (170 gallons) was treated batchwise with Amberlite XAD-2 resin (17 gallons). After stirring for one hour, the suspension was filtered through a bed of filtering-aid.

The mycelial-resin cake was extracted twice in succession with 90 and 60 gallons of acetone, stirring for two hours at ambient temperature. After filtration, the extracts were combined and concentrated under reduced pressure to an oil.

One-half of this oil was adsorbed onto 180 g of silica gel by stirring; after washing the silica gel with petroleum ether on a filtering funnel, the adsorbent was poured carefully onto the top of a silica gel chromatography column packed with 2 kg of silica gel 230–400 mesh. The column was washed with 10 liters of methylene chloride which removed most of the nonpolar impurities. The compound of interest was eluted from the column with methylene chloride-methanol (9:1 v/v). The appropriate fractions were united and concentrated down to an oil in preparation for the next purification step.

Further fractionation was achieved by passing this oil through another silica gel column (7 liters, packed in and equilibrated with methylene chloride-methanol 95:5 v/v). Elution with the same solvent afforded component D after 2.0 column volumes. Final purification was performed by reverse-phase HPLC (Whatman ODS-3 Magnum 9 column) eluting with 25% by volume acetonitrrle in water at 10.0 ml/min.

Component D was obtained pure between approximately 5.5 and 6.5 column volumes of eluate.

EXAMPLE 9

Synthesis of Minor Component D

Oxidation of the compound of Formula I was conducted by the reaction of 0.056 mmole Formula I compound witn 0.133 mmole m-chloroperbenzoic acid in 10 ml methylene chloride at room temperature for 30 minutes.

The reaction mixture was worked up by diluting with 30 ml methylene chloride, and repeated (3x) washes with an equivalent amount of dilute (5%) sodium bicarbonate solution. The organic solvent was removed in vacuo and the residue purified by gel filtration chromatography on Sephadex LH-20 in methanol.

The isolated N-(Leu)-hydroxylamine derivative of the compound of Formula I was identical to the natural minor component D as characterized by tlc, HPLC and mass spectrometry.

EXAMPLE 10

Synthesis of Minor Component D

The compound of Formula I (1.0 mmole), m-chloroperbenzoic acid (2.4 mmole) in 80 ml methylene chloride and 9 ml glacial acetic acid was stirred at room temperature for between 2 to 3 hours.

The reaction mixture was worked up as in Example 9.

The desired compound was purified by repeated column chromatography on silica gel eluting with (a) ethyl acetate; and (b) methylene chloride-methanol (97:3 v/v). Further purification was accomplished by reversed-phase HPLC eluting with 30–40% acetonitrile in water.

The isolated compound compared favorably with the compound from Example 9 and the natural minor component D.

It is anticipated that other oxidizing agents could also be used to effectuate the transformation of the compound of Formula I to the minor component D. For example, peroxyacids such as peroxyacetic, peroxybenzoic or mono-peroxyphthalic acids; hydrogen peroxide, and other oxidizing agents available to the skilled artisan could be usec in place of the m-chloroperbenzoic acid of Examples 9 and 10.

Characterization of the Compound of Formula I

The solid material obtained in Example 6 was characterized by high resolution mass spectrometry, nuclear magnetic resonance spectroscopy (i.e. proton and carbon-13), infrared and ultraviolet spectroscopy and optical rotation as discussed below. From these data, the structure I was assigned:

1. Mass Spectral Data

The Example 6 sample exhibited a molcular ion in its electron impact mass spectrum (EI-MS) at m/e 535 corresponding to the molecular formula $C_{31}H_{29}N_5O_4$ by high resolution mass measurement (calc. for $C_{31}H_{29}N_5O_4$ 535.2220, found 535.2205). FAB (Fast Atom Bombardment) analysis of the Example 6 sample corroborate the EI-MS molecular weight assigment (observed $(M+H)^+$, m/e 536). Upon derivitization with bis-trimethylsilyltrifluoroacetamide (BSTFA), a di-TMS derivative is formed ($M^+$ observed H-TMS, m/e 679; D-TMS, m/e 697).

Significant ions in the EI-MS of the compound of Formula I and their exact mass values and corrsponding elemental formula are shown in Table II.

TABLE II

| Electron Impact-Mass Spectrum Data | | |
|---|---|---|
| Found | Calc. | Formula |
| 86.0972 | 86.0970 | $C_5H_{12}N$ |
| 130.0299 | 130.0293 | $C_8H_4NO$ |
| 146.0606 | 146.0606 | $C_9H_8NO$ |
| 213.1419 | 213.1392 | $C_{14}H_{17}N_2$ |
| 235.0846 | 235.0871 | $C_{15}H_{11}N_2O$ |
| 241.1355 | 241.1341 | $C_{15}H_{17}N_2O$ |
| 249.0671 | 249.0664 | $C_{15}H_9N_2O_2$ |
| 259.1486 | 259.1447 | $C_{15}H_{19}N_2O_2$ |
| 275.0836 | 275.0821 | $C_{17}H_{11}N_2O_2$ |
| 277.0869 | 277.0851 | $C_{16}H_{11}N_3O_2$ |
| 292.1117 | 292.1086 | $C_{17}H_{14}N_3O_2$ |
| 404.1248 | 404.1273 | $C_{25}H_{16}N_4O_2$ |
| 422.1397 | 422.1379 | $C_{25}H_{18}N_4O_3$ |
| 478.1504 | 478.1515 | $C_{27}H_{20}N_5O_4$ |
| 517.2101 | 517.2114 | $C_{31}H_{27}N_5O_3$ |
| 535.2205 | 535.2220 | $C_{31}H_{29}N_5O_4,M^+$ |

Extensive linked-scan metastable analysis of significant ions in the mass spectrum of the neat sample from Example 6 disclosed fragmentation pathways which, in conjunction with the NMR data, allowed assignment of the structure (I) for the compound.

The structure I as shown above is intended to encompass all possible stereoisomers.

2. $^{13}C$ NMR Chemical Shifts

The carbon-13 spectrum of the sample from Example 6 was recorded in $CDCl_3$ at 25° C. (35 mg/0.35ml). Chemical shifts are in ppm downfield of internal tetramethylsilane (TMS) standard. In agreement with the mass spectral data, 31 carbon atoms are observed with the following chemical shifts: 21.5, 23.6, 25.2, 34.2, 42.8, 50.9, 62.0, 81.4, 87.0, 116.3, 121.6, 124.2, 125.8, 127.7, 127.9, 128.0, 128.8, 129.3, 129.9, 130.0, 130.4, 131.9, 133.8, 135.3, 136.7, 139.2, 146.3, 155.5, 162.2, 168.5, 171.2 ppm.

3. Proton NMR spectrum

Figure 1:
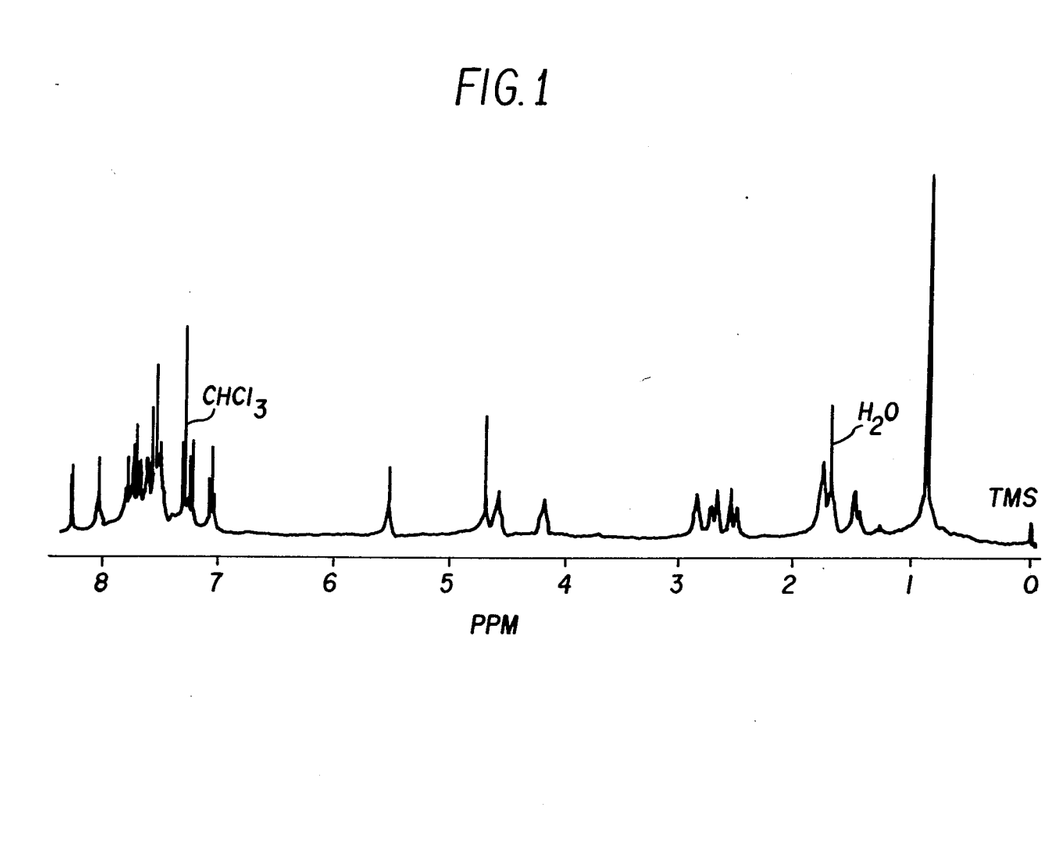
FIG. 1 is a proton nuclear magnetic resonance (NMR) spectrum of the compound of Formula I.

See FIG. 1. The proton NMR spectrum was recorded in $CDCl_3$ solution at 25° C. Chemical shifts are shown in ppm relative to internal tetramethylsilane at zero ppm.

4. Infrared spectrum

Figure 2:
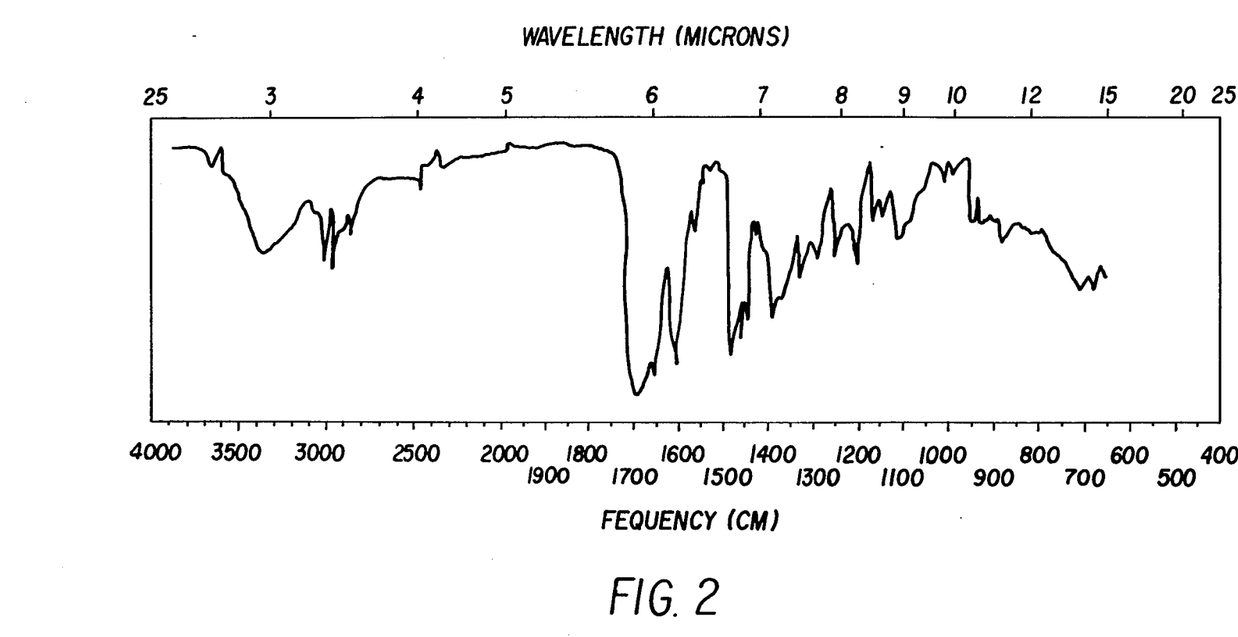
FIG. 2 is an infrared (IR) spectrum of the compound of Formula I.

See FIG. 2. The spectrum was recorded in chloroform solution.

5. Ultraviolet spectrum

Figure 3:
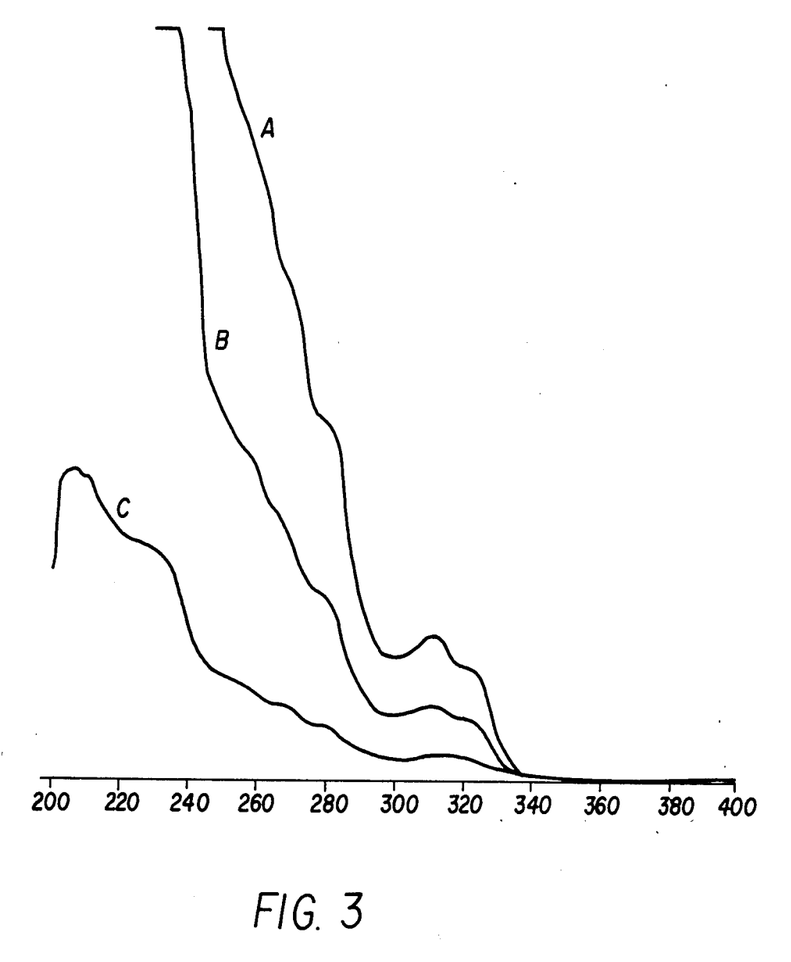
FIG. 3 is an ultraviolet (UV) spectrum of the compound of Formula I.
Figure 4:
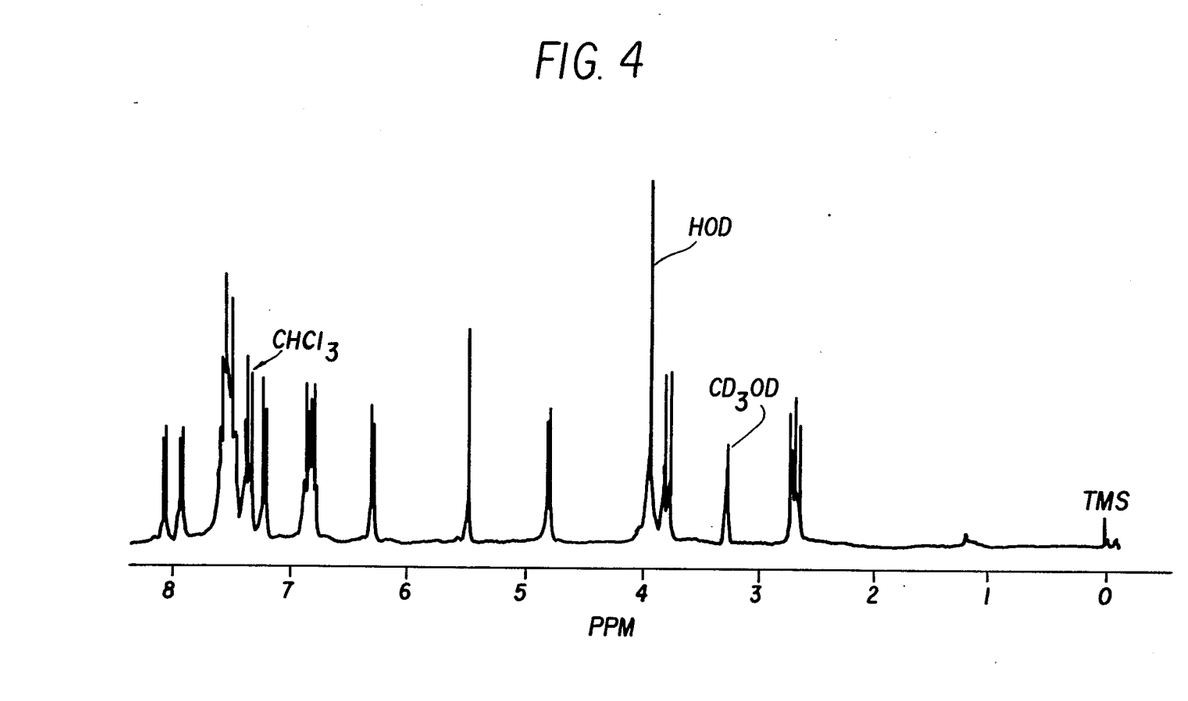
FIG. 4 is a proton NMR spectrum of minor component A.
Figure 5:
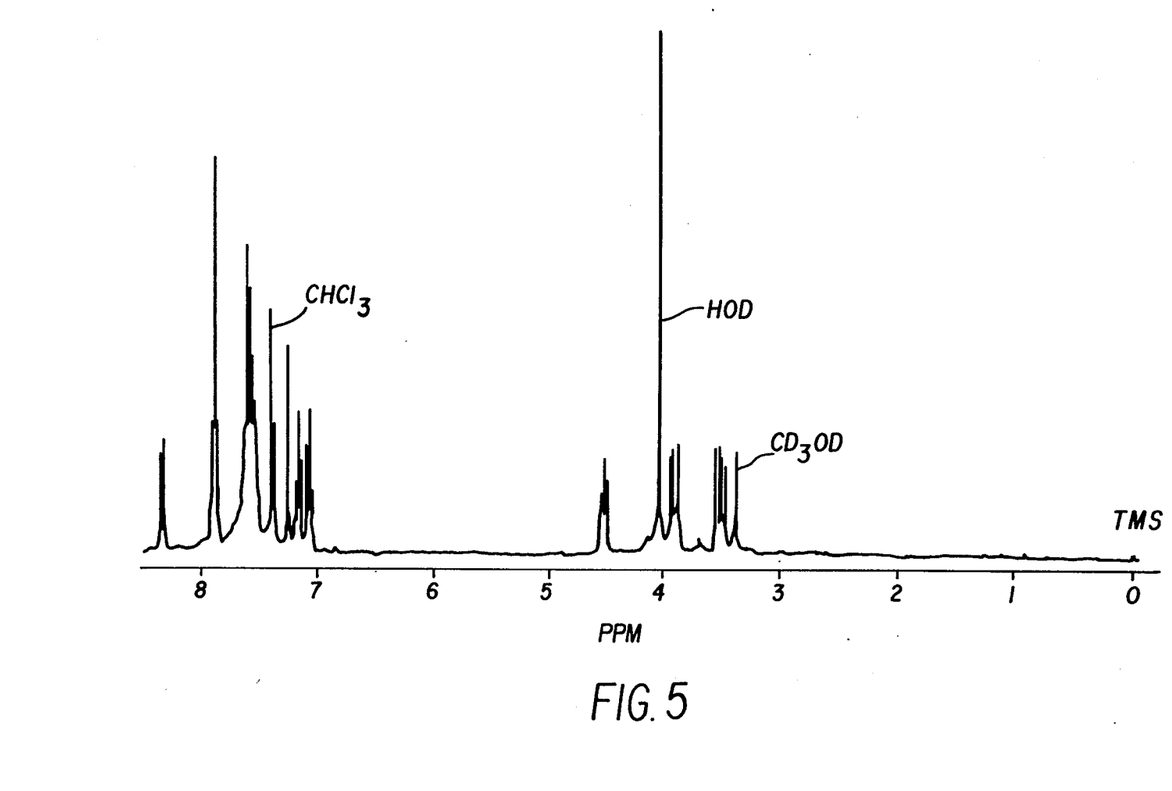
FIG. 5 is a proton NMR spectrum of minor component B.
Figure 6:
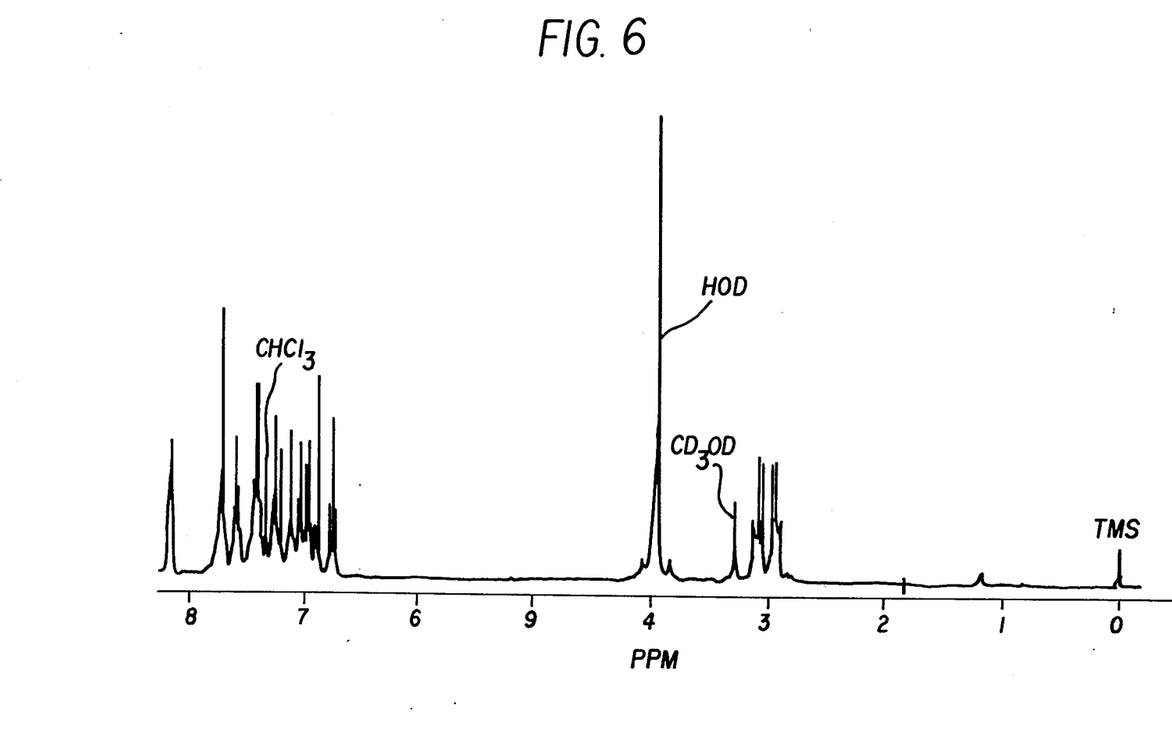
FIG. 6 is a proton NMR spectrum of minor component C.
Figure 7:
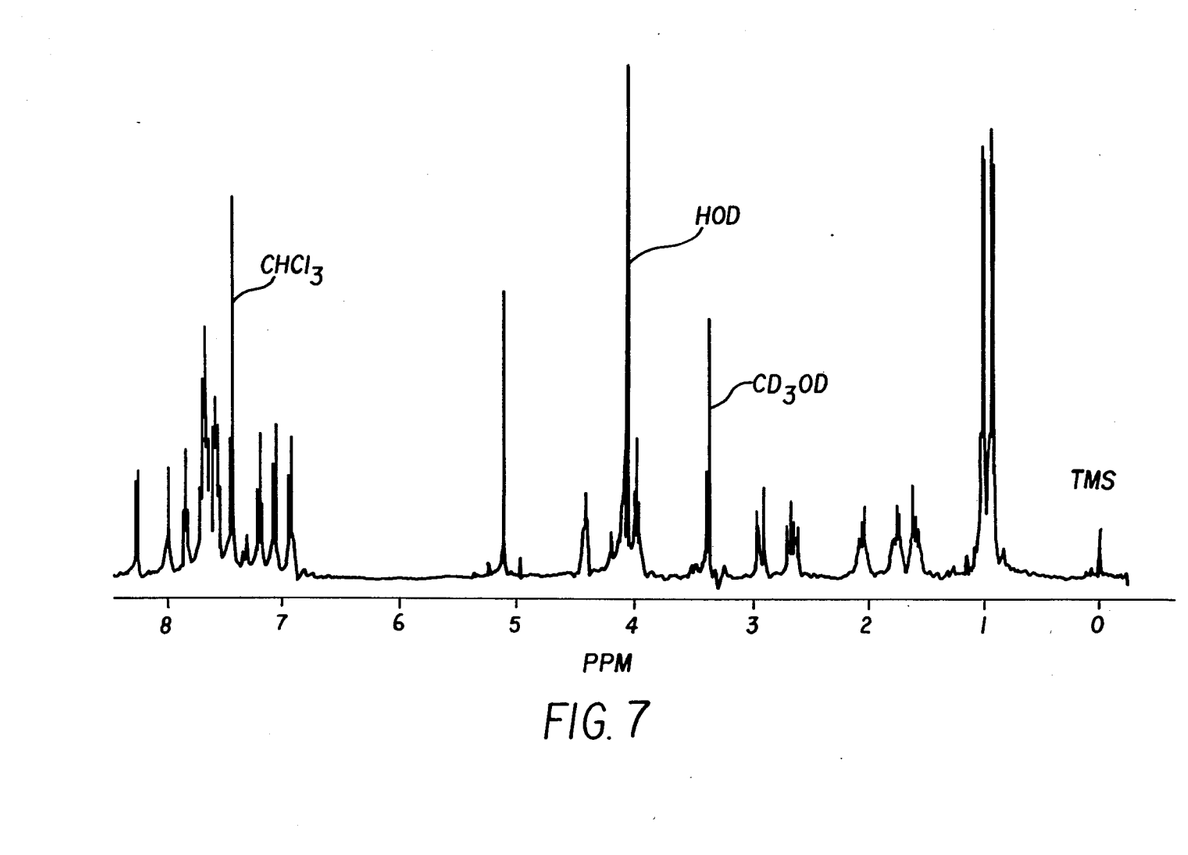
FIG. 7 is a proton NMR spectrum of minor component D.

The ultraviolet absorption spectrum of the compound of Formula I was measured on a solution of 1.280 mg n: A) 50 ml, B) 100 ml and C) 400 ml of methanol (see curves A, B and C in FIG. 3. A maximum was observed at 310.5 nm (4075) and shoulders near 322 nm ($\epsilon$ 3135), 278 nm ($\epsilon$ 10,350), 266 nm ($\epsilon$ 14,420), 258 nm ($\epsilon$ 17,760), 230 nm ($\epsilon$ 48,490).

6. Optical Rotation

The specific optical rotation, $[\alpha]_D^{26.5}$ of $-185.3°$ was determined on a solution of 13.185 mg/1.2 ml of methanol solution. The value was measured at the sodium-D-line wavelength.

7. Specific Sterochemistry

The specific sterochemistry of the compound of Formula I was obtained by X-ray crystallography of the hydrochloride:

Characterization of the Minor components

The minor compounds A, B and C, isolated in Example 7 and component D, isolated in Example 8, were analyzed by nuclear magnetic resonance (NMR) spectroscopy, ultraviolet spectroscopy and/or high resolution mass spectrometry. The NMR spectra of the minor components are reproduced in FIGS. 4–7. The spectra were recorded in 20% CD$_3$0D/CDCl$_3$ at ambient temperature. Chemical shifts are shown in ppm relative to internal tetramethylsilane at zero ppm. The solubility characteristics of components A–D are similar to those of the compound of Formula I; soluble in: CHCl$_3$, MeOH, EtOH, acetone, DMSO;

insoluble in: H$_2$O, hexane, pet. ether.

High performance liquid chromatography (HPLC) of the fermentation broth of *Aspergillus alliaceus* Thom and Church, ATCC No. 20655 or 20656 is useful in distinguishing the compound of Formula I from its minor components. Capacity factors for the isolated components are quite different. Capacity factor is an HPLC retention time factor defined as follows:

$$\text{Capacity factor} = \frac{R \text{ compound} - R \text{ known}}{R \text{ known}}$$

wherein:

R compound = HPLC retention time of the compound of interest

R known = HPLC retention time of an *unretained* compound, e.g., MeOH.

Capacity factors for the compound of Formula I and the minor components A–D are as follows:

| Formula I | 5.3 |
|---|---|
| A | 3.0 |
| B | 6.5 |
| C | 7.7 |
| D | 4.9 |

1. Compound A

The ultraviolet absorption spectrum of compound A in methanol, showed the following pattern (nm): 213 sh, 227, 268, 277 sh, 310 sh and 324.

The high resolution mass spectrum of component A suggests a molecular formula of C$_{25}$H$_{18}$N$_4$O$_3$. The mass spectral fragmentation pattern is as follows:

| FOUND | CALC | FOR |
|---|---|---|
| 422.1376 | 422.1379 | M+, C$_{25}$H$_{18}$N$_4$O$_3$ |
| 404.1224 | 404.1273 | C$_{25}$H$_{16}$N$_4$O$_2$ |
| 285.0894 | 285.0902 | C$_{18}$H$_{11}$N$_3$O |
| 275.0823 | 275.0820 | C$_{17}$H$_{11}$N$_2$O$_2$ |
| 247.0883 | 247.0871 | C$_{16}$H$_{11}$N$_2$O |
| 234.0797 | 234.0793 | C$_{15}$H$_{10}$N$_2$O |
| 146.0590 | 146.0606 | C$_9$H$_8$NO |
| 146.0221 | 146.0242 | C$_8$H$_4$NO$_2$ |
| 130.0298 | 130.0293 | C$_8$H$_4$NO |
| 130.0654 | 130.0657 | C$_9$H$_8$N |
| 120.0432 | 120.0449 | C$_7$H$_6$NO |
| 102.0376 | 102.0344 | C$_7$H$_4$N |

The mass spectral data combined with the NMR data (see FIG. 4, 20% CD$_3$OD/CDCl$_3$ solution) allowed the assignment of the following structure:

2. Component B

The ultraviolet absorption spectrum of component B in methanol showed the following pattern (nm): 222, 268, 278, 289 sh.

The high resolution mass spectrum of component B suggests a molecular formula of C$_{25}$H$_{18}$N$_4$O$_2$. The mass spectral fragmentation pattern is as follows:

| FOUND | CALC. | FOR |
|---|---|---|
| 406.1438 | 406.1430 | M+, C$_{25}$H$_{18}$N$_4$O$_2$ |
| 286.0970 | 286.0980 | C$_{18}$H$_{12}$N$_3$O |
| 277.0845 | 277.0851 | C$_{16}$H$_{11}$N$_3$O$_2$ |
| 260.0939 | 260.0950 | C$_{17}$H$_{12}$N$_2$O |
| 249.0676 | 249.0664 | C$_{15}$H$_9$N$_2$O$_2$ |
| 158.0852 | 158.0844 | C$_{10}$H$_{10}$N$_2$ |
| 130.0671 | 130.0657 | C$_9$H$_8$N |

The mass spectral data combined with the NMR data (see FIG. 5, 20% CD$_3$OD/CDCl$_3$ solution) allowed the assignment of the following structure:

3. Compound C

The ultraviolet absorption spectrum of compound C in methanol showed the following pattern (nm): 222, 283 sh, 290.

The high reslolution mass spectrum of component C suggests a molecular formula of $C_{25}H_{18}N_4O_2$. The mass spectral fragmentation pattern is as follows:

| FOUND | CALC | FOR |
| --- | --- | --- |
| 406.1407 | 406.1430 | M+, $C_{25}H_{18}N_{24}O_2$ |
| 388.1318 | 388.1324 | $C_{25}H_{16}N_4O$ |
| 362.1271 | 362.1293 | $C_{24}H_{16}N_3O$ |
| 277.0833 | 277.0851 | $C_{16}H_{11}N_3O_2$ |
| 237.0899 | 237.0902 | $C_{14}H_{11}N_3O$ |
| 223.0883 | 223.0871 | $C_{14}H_{11}N_2O$ |
| 184.0655 | 184.0637 | $C_{11}H_8N_2O$ |
| 170.0601 | 170.0606 | $C_{11}H_8NO$ |
| 130.0671 | 130.0657 | $C_9H_8N$ |

The mass spectral data combined with the NMR data (see FIG. 6, 20% $CD_3OD/CDCl_3$ solution) allowed the assignment of the following structure:

4. Compound D

The high resolution mass spectrum of component D suggests a molecular formula of $C_{31}H_{29}N_5O_5$. The fragmentation pattern is as follows:

| FOUND | CALC | FOR |
| --- | --- | --- |
| 551.2145 | 551.2169 | M+, $C_{31}H_{29}N_5O_5$ |

The mass spectral data combined with the NMR data (see FIG. 7, 20% $CD_3OD/CDCl_3$ solution) allowed the assignment of the following structure:

In Vitro Activity of Formula I

The biological activity of the compound of Formula I was evaluated using an $^{125}I$-CCK receptor binding assay and in vitro isolated tissue preparations.

Materials and Methods

1. CCK receptor binding

CCK-33 was radiolabeled with 125I-Bolton Hunter reagent (2000 Ci/mmole) as described by Sankara et al. (J. Biol. Chem. 254: 9349-9351, 1979). Receptor binding was performed according to Innis and Snyder (Proc. Natl. Acad. Sci. 77:6917-6921, 1980) with the minor modification of adding the additional protease inhibitors, phenylmethane sulfonyl fluoride and o-phenanthroline. The latter two compounds have no effect on the $^{125}I$-CCK receptor binding assay.

Male Sprague-Dawley rats (200-350g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline). For the binding assay, 25 µl of buffer (for total binding) or unlabeled CCK-8 sulfate to give a final concentration of 1µM (for nonspecific binding) or the compound of Formula I (for determination inhibition of $^{125}I$-CCK binding) and 25 µl of $^{125}I$-CCK-33 (30,000-40,000 cpm) were added to 450 µl of the membrane suspensions in microfuge tubes. All assays were run in duplicate or triplicate. The reaction mixtures were incubated at 37° C. for 30 minutes and centrifuged n a Beckman Microfuge (4 minutes) immediately after adding 1 ml of ice-cold incubation buffer. The supernatant was aspirated and discarded, pellets were counted with a Beckman gamma 5000. For Scatchard analysis (Ann. N. Y. Acad. Sci. 51: 660, 1949), $^{125}I$-CCK-33 was progressively oiluted with increasing concentrations of CCK-33.

2. Isolated guinea pig qall bladder

Male Hartley guinea pigs (400-600 g) were sacrificed by decapitation. The whole gall bladder was dissected free from adjacent tissues and its content gently squeezed out. The whole bladder was suspended in 5 ml organ bath under 1 g tension. The organ bath contained a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions were recorded using Statham (60 g; 0.12 mm) strain gauges and a Hewlett-Packard (77588) recorder. The tissues were washed every 10 minutes for 1 hr to obtain equilibrum prior to the beginning of the study. CCK-8 was added cumulatively to the baths and $EC_{50}$'s determined using regression analysis. After washout (every 10 minutes for 1 hr), the compound of Formula I was added at least 5 minutes before the addition of CCK-8 and the $EC_{50}$ of CCK-8 n the presence of the compound of Formula I similarly determined. The $pA_2$ values ano slope were obtained from regression analysis of a Schild plot (Brit. J. Pharmacol. 14: 48-58, 1959) using three concentrations of the compound of Formula I and 3-4 tissues at each concentration.

3. Isolated longitudinal muscle of guinea pig ileum

Longitudinal muscle strips with attached nerve plexus were prepared as described previously (Brit. J. Pharmac. 23; 356-363, 1964; J. Physiol. 194 13-33, 1969). Male Hartley guinea pigs were decapitated and the ileum was removed (10 cm of the terminal ileum was discarded and the adjacent 20 cm piece was used). A piece (10 cm) of the ileum was stretched on a glass pipette. Using a cotton applicator to stroke tangently away from the mesentery attachment at one end, the longitudinal muscle was separated from the underlying circular muscle. The longitudinal muscle was then tied to a thread and by gently pulling, stripped away from the entire muscle. A piece of approximately 2 cm was suspended in 5 ml organ bath containing Krebs solution and bubbled with 95% $O_2$ and 5% $CO_2$ at 37° C. under 0.5 g tension. CCK-8 was added cumulatively to the baths nd $EC_{50}$ and $pA_2$ values determined as described in the gall bladder preparation (above)

In Vitro Results

1. Effect of The Compound of Formula I on $^{125}$I-CCK-33 receptor binding

The compound of Formula I inhibited specific $^{125}$I-CCK-33 binding in a concentration dependent manner with an $IC_{50}$ of 0.7 ug/ml (1.3 $\mu M$). Scatchard analysis of specific $^{125}$I-CCK-33 receptor binding in the absence and presence of 1.3 $\mu M$ of the compound of Formula I indicated the compound of Formula I competitively inhibited specific $^{125}$I-CCK-33 receptor binding since it increased the $K_D$ (dissociation constant) without affecting the $B_{max}$ (maximum receptor number) The $K_i$ value (dissociation constant of inhibitor) of the compound of Formula I was estimated to be 0.9 $\mu M$.

2. Effect of The Compound of Formula I on isolated gall bladder of guinea pig

The compound of Formula I (1.3-13 uM) caused a concentration dependent parallel shift to the right of the CCK-8 dose-response without change in the maximal contractile response. The Schild plot gave a $pA_2$ value of 6.0±0.2 corresponding to $K_i$ value of 1 $\mu M$ and which was in good agreement with the $K_i$ value obtained from $^{125}$I-CCK binding studies (see above). The slope of the Schild plot (0.95±0.19) did not differ significantly from unity indicating the compound of Formula I acts as a competitive antagonist of CCK-8 in this preparation 3. Effect of The Compound of Formula I on the isolated guinea pig lonqitudinal muscle The compound of Formula I (1.3-13 $\mu M$) caused a concentration dependent parallel shift to the right of the CCK-8 dose-response without change in the maximal contractile response The Schild plot gave a $pA_2$ value of 6.4±0.4 corresponding to $K_i$ of 0.4 $\mu M$ which was in good agreement wth the $K_i$ value obtained from binding studies and the guinea pig gall bladoer (see above). The slope of the Schild plot did not differ significantly from unity (0.89±0.20) indicating competitive antagonism of CCK by the compound of Formula I.

The minor components A-D have also been tested for their capacity to antagonize CCK. Based on tne activity of the compound of Formula I, the minor components relative activities are:

I: 1×
A: 1/70×
B: 1/7×
C: 1/30×
D: 5×

The ability of the compound of Formula I and its minor related compounds to antagonize CCK makes these compounds useful as pharmaceutical agents. These compounds will be especially useful in the treatment and prevention of disease states wherein CCK may be involved, for example, gastrointestinal disorders such as irritable bowel syndrome, ulcers, acute pancreatis, motility disorders, central nervous system disorders caused by CCK's interaction with dopamine such as neuroleptic disorders, tardive dyskinesia, Parkinson's disease, psychosis or Gilles de la Tourette Syndrome, and disorders of the appetite regulatory systems.

The compound of Formula I and its minor related compounds or a pharmaceutically acceptable salt thereof, can be administered to a human subject either alone, or preferably, in combination with pharmaceutically acceptable carriers or diluents, in a pharmaceutical composition, according to standard pharmaceutical practice. The compound can be administered orally or parenterally. Parenteral administration includes intravenous, intramuscular, intraperitoneal, subcutaneous and topical administration.

For oral use of an antagonist of CCK of tnis invention, the selected compound can be administered, for example, in the form of tablets or capsules, or as an aqueous solution or suspension. In the case of tablets for oral use, carriers which are commonly used includoe lactose and corn starch, and lubricating agents, such as magnesium stearate, are commonly added. For oral administration in capsule form, useful diluents are lactose and dried corn starch When aqueous suspensions are required for oral use, the active ingredient s combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When tne compound of Formula I and its minor related compounds or a salt thereof is used as an antagonist of CCK in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 1 mg to about 1500 mg and preferably 10 mg to 500 mg in a single or divided doses. On the other hand, it may be necessary to use dosages outside these limits in some cases.

Claims to the invention follow.

What is claimed is:

1. A process for preparing the compund of Formula I;

and its minor related components A, B, C and D which comprises the aerobic fermentation of a strain of *Aspergillus alliaceus* Thom and Church that is capable of producing said compound and its minor related components A, B, C and D wherein said aerobic fermentation is under operating conditions and a time period that are controlled so as to produce a recoverable amount of said compound or one of its minor related components A, B, C, and D in an assimilable aqueous nutrient medium and isolating at least one of said compound and its minor related components A, B, C and D.

2. The process of claim 1 wherein the controlled aerobic fermentation is at a temperature range of from 20° to 37° C. for at least 24 hours.

3. The process of claim 1 wherein the strain of *Aspergillus alliaceus* Thom and Church is selected from the group consisting of ATCC No. 20655 and ATCC No. 20656.

4. The process of claim 1 wherein the controlled aerobic fermentation is at 28° C. for about 144 hours.

5. The process of claim 1 wherein the isolation of the compound of Formula I is accomplished by an extraction step followed by a chromatographic separation step.

6. The process of claim 5 wherein the chromatographic step comprises the sequential chromatographic steps of:
(a) silica gel chromatography;
(b) gel permeation chromatography;
(c) reverse phase high pressure liquid chromatography.

* * * * *